United States Patent [19]

Carr et al.

[11] 4,128,591

[45] Dec. 5, 1978

[54] ALKYL AROMATIC ISOMERIZATION

[75] Inventors: William C. Carr, Weehawken; Leon M. Polinski, North Plainfield; Saul G. Hindin, Mendham; James L. Kosco, Fanwood, all of N.J.

[73] Assignee: Engelhard Minerals & Chemicals Corporation, Iselin, N.J.

[21] Appl. No.: 802,204

[22] Filed: May 31, 1977

[51] Int. Cl.² ............................................. C07C 15/08
[52] U.S. Cl. .............................. 260/668 A; 260/668 R; 252/455 Z
[58] Field of Search ...................... 260/668 A, 668 R; 252/455 Z

[56] References Cited

U.S. PATENT DOCUMENTS

| 3,409,686 | 11/1968 | Mitsche | 260/668 A |
| 3,767,721 | 10/1973 | Sonoda et al. | 252/455 Z |

Primary Examiner—Veronica O'Keefe

[57] ABSTRACT

Disclosure is made of an improved catalyst and process for producing a near equilibrium mixture of xylenes from a feedstream comprising ethylbenzene and mixed xylenes. The catalyst combines a platinum-containing hydrogenation-dehydrogenation component on an alumina support with a form of hydrogen mordenite having less than about 0.3 equivalents of alkali and alkaline earth metal cations per gram-atom of aluminum and a silica to alumina mol ratio greater than about 9–11 to 1 and less than about 17 to 1.

2 Claims, No Drawings

ALKYL AROMATIC ISOMERIZATION

BACKGROUND OF THE INVENTION

The invention relates in general to a catalyst and process for the isomerization of alkyl aromatics. In particular, the invention relates to improvements in the commercial processes in which a mixture of xylenes and ethylbenzene are reacted along with hydrogen over a platinum-containing catalyst to produce a near equilibrium mixture of xylenes while converting ethylbenzene to xylenes.

Isomerization of alkyl aromatics has become particularly important commercially. In processes for the production of xylenes, the ortho and paraxylenes are the preferred products. Paraxylene is principally used in preparation of polyesters while orthoxylene's main end use is in preparation of phthalic anhydride. Metaxylene has fewer important end uses and thus it may be converted to the para and ortho forms, which have greater commercial value. After paraxylene and orthoxylene have been separated as products, it is typical that metaxylene is recycled to the isomerization reactor along with unreacted ethylbenzene, residual amounts of orthoxylene and paraxylene, and naphthenes. Thus the combined isomerization and separation steps produce the desired products and the remaining $C_8$ compounds are recycled to extinction.

Ethylbenzene is difficult to separate from the xylenes since their boiling points are very close. Accordingly, ethylbenzene is normally present within the mixture of xylenes prepared by extraction or distillation from a hydrocarbon stream. There are two approaches commonly taken in the prior art to handle the ethylbenzene contained in a mixed xylene stream, which may be present in the range of 15-65 wt.%, which is greater than the equilibrium amount. Generally, ethylbenzene is not easily isomerized and many processes have chosen to remove the ethylbenzene by destroying it through disproportionation, hydrodealkylation or the like to yield lighter and heavier compounds which can be easily separated by distillation from the $C_8$ compounds. It will be apparent that such processes dispose of a significant quantity of potential xylenes by such reactions. Typical processes of the prior art which remove ethylbenzenes by destruction are U.S. Pat. Nos. 3,856,871-4 in which special zeolite molecular sieves are used to isomerize xylenes while converting ethylbenzene to $C_6$, $C_7$, $C_9$, $C_{10}$ aromatic compounds and non-aromatics.

It is also known in the prior art to react ethylbenzene to form xylenes in the presence of hydrogen and a hydrogenation-dehydrogenation catalyst, preferably platinum on alumina. Typical of the prior art is U.S. Pat. No. 2,976,332 which discloses a catalyst comprising platinum on alumina plus an amorphous silica alumina to convert ethylbenzene and isomerize xylenes, with a minimum of side reactions which reduce yield selectivity and contribute to catalyst aging. Platinum provides the hydrogenation-dehydrogenation function believed to be required for the probable reaction mechanism for converting ethylbenzene. Catalysts of this type have been commercially used with considerable success.

When ethylbenzene is not present, conversion of xylenes alone has been found to be possible with many catalysts, which include an amorphous silica alumina, hydrogen mordenite, dealkalized mordenite, and special zeolites. In the case of the zeolites, it has been common in the prior art to prepare zeolites in the sodium form and thereafter to replace sodium with other cations or hydrogen ions in order to improve performance.

Combination catalysts which are capable of isomerizing xylenes and ethylbenzenes to approach an equilibrium distribution of isomers include that of U.S. Pat. No. 2,976,332 mentioned above which combines platinum on alumina with amorphous silica alumina. More recent combination catalysts are disclosed in U.S. Pat. No. 3,409,686 in which alumina gel is mixed with particles of hydrogen mordenite to form a mixed base which is, after drying, impregnated with a platinum solution. Another mixed catalyst is illustrated in U.S. Pat. No. 3,767,721 in which platinum on alumina in a fine powder form is combined with powdered mordenite. It is shown that hydrogen mordenite in such a combination is overly active and promotes destructive reactions which are undesirable. Accordingly, the patent discloses and claims a process in which the catalyst is a partially dealkalized mordenite, rather than hydrogen mordenite. The content of alkali and alkaline earth metals in the mordenite is adjusted so that destructive reactions are minimized.

In summary, the prior art discloses a number of catalysts for isomerization of xylenes alone and combination catalysts for isomerization of xylenes combined with conversion of ethylbenzenes to xylenes. Specifically with relation to the present invention, the prior art teaches that hydrogen mordenite is useful for isomerization of xylenes. In addition, the art teaches that hydrogen mordenite may be combined with an alumina gel to form a mixed base, which is thereafter inpregnated with a platinum solution. Another catalyst in the prior art employs a segregated base wherein the platinum is deposited only on the alumina portion and thereafter the platinum on alumina is combined with a dealkalized form of mordenite rather than hydrogen mordenite. In such a catalyst, the art teaches that the hydrogen form of mordenite produces an overly active catalyst. Finally, the prior art teaches that a segregated base may also be used in which platinum is deposited on an alumina and thereafter combined with amorphous silica alumina, both being in the finely divided powder form.

While some of the prior art catalysts have been successful in isomerizing xylenes and ethylbenzene, further improvement has been desired in order to achieve a highly selective catalyst which can be operated to approach chemical equilibrium in the isomerization of xylenes and ethylbenzene while at the same time avoiding the destructive reactions which can result in a loss of $C_8$ aromatics. In addition, maintenance of activity and selectivity for longer periods than heretofore possible is desirable. Such an improved catalyst is described below.

SUMMARY OF THE INVENTION

An improved catalyst for the isomerization of alkyl aromatics, particularly combined xylenes and ethylbenzenes, may be formed by depositing platinum on alumina and thereafter combining the platinum-alumina with a form of hydrogen mordenite containing less than about 0.3 equivalents of alkali and alkaline earth metal cations per gram atom of aluminum (preferably less than 0.1) and having a silica to alumina ratio greater than the nominal range of about 9:1 to 11:1, preferably in the neighborhood of about 14:1, but less than about 17:1. Both the platinum containing alumina and the hydrogen mordenite are prepared as finely divided particulates and thereafter combined to produce the finished catalyst. Additional amounts of alumina, amorphous silica-alumina, or the like may be included in some compositions of the invention as a binder or diluent. The platinum may be used in combination with palladium, ruthenium, rhodium, iridium, and rhenium. Both alumina and hydrogen mordenite particles are within the range of submicron to 50 microns. In one preferred embodiment of the invention, the alumina particles are in the range of 1 to 10 microns and the hydrogen mordenite particles are in the range of 1 to 20 microns.

The composition of catalysts of the invention is within the broad limits of 0.1–1 wt.% platinum, 10–85 wt.% alumina support for platinum, 1–65% hydrogen mordenite, and 0–80 wt.% binder or diluent.

In preferred catalysts the alumina support will be in the range of about 20–60 wt.%, the hydrogen mordenite will be within the range of about 20–60 wt.% and the platinum will be in the range of 0.3–0.4 wt.%, all based on the finished catalyst. When additional alumina or amorphous silica-alumina is included as binder or diluent, amounts up to 60% by weight of the finished catalyst may be used.

The catalyst of the invention may be prepared in several ways, the common denominator among them being that platinum is deposited on the alumina before hydrogen mordenite is mixed with the platinum-alumina combination, which is believed to minimize migration of platinum from the alumina to the hydrogen mordenite.

The catalyst of the invention is particularly useful in providing improved performance in processes which isomerize both ethylbenzene and xylenes in the presence of hydrogen, while minimizing destructive reactions which provide undesired compounds.

DESCRIPTION OF THE PREFERRED EMBODIMENTS

Catalyst Composition

As will be shown hereafter through comparative examples, it has been found that a combination of components is able to accomplish the isomerization of both xylenes and ethylbenzene. Single components ordinarily cannot isomerize both xylenes and ethylbenzene satisfactorily, as will be evident from the examples. As will be seen also, the method of combining the individual components of the catalyst is an important aspect of the invention.

The catalyst of the invention is composed of three basic components: a support, a platinum-containing hydrogenation-dehydrogenation catalyst deposited on the support, and a form of hydrogen mordenite. For the support, aluminas are preferred. As will be seen hereafter, alumina in predominantly the eta and gamma forms may be used successfully.

For producing a highly active and selective catalyst for $C_8$ isomerization, hydrogen mordenite particles will be in the range of 1–20 microns and alumina particles in the range of 1–40 microns.

Platinum alone may be used as the hydrogenation-dehydrogenation component, although palladium, ruthenium, rhodium, iridium, and rhenium may be included. While the usable range is 0.1–1 wt.%, the optimum amount of the hydrogenation-dehydrogenation component appears to be in the range of 0.3–0.4 wt.% of the finished catalyst. The amount used is determined by its effectiveness in the finished catalyst. Smaller amounts tend to produce catalysts which lose activity and selectivity rapidly and which have a shorter useful life; larger amounts do not give sufficient improvement to offset the additional cost. However, either smaller or larger amounts could be used if one were willing to accept the associated disadvantages.

Platinum may be deposited on the alumina support by various methods, including adsorption by an alumina slurried in a solution of a water soluble salt of platinum and absorption of such solutions by a dry powdered alumina. Following deposition of the platinum, it is usually fixed in place on the support, as by treatment with hydrogen sulfide, reduction to metallic platinum or oxidation by calcination. After fixing the platinum, the platinum on alumina is mixed with a form of hydrogen mordenite. As will be seen hereafter, the performance of a catalyst in which platinum is deposited solely on the alumina is substantially better than one in which a combined base of alumina and hydrogen mordenite is impregnated with platinum.

The third ingredient of the catalyst of the invention is a form of hydrogen mordenite. A synthetic hydrogen mordenite commercially available from the Norton Company, Zeolon®, has been found to produce a highly effective catalyst. The synthesis of such mordenite has been described and claimed in U.S. Pat. No. 3,436,174. The theoretical ratio of silica to alumina in this synthetic mordenite is given as 9–10 to 1 in the patent. However, as synthesized, synthetic mordenite is typically found to have a nominal silica to alumina ratio of 9–11 to 1, and this nominal ratio will be used hereinafter in referring to the commercially available material. The mordenite may be dealuminized by acid treatment to increase the silica to alumina ratio, as described also in U.S. Pat. No. 3,436,174. Hydrogen mordenites having a silica to alumina ratio above the nominal 9–11 to 1 but less than about 17 to 1 are used in catalysts according to the invention and may have a particle size of approximately 1–20 microns.

The catalyst may contain ingredients having no substantial catalytic effect. In particular, alumina or silica-alumina have been used as binders or diluents as will be seen in the examples which follow.

It is known in the prior art that the ratio of aluminum atoms to sodium or other cations affects the activity of mordenite for catalyst reactions. In particular, U.S. Pat. No. 3,767,721 indicates that for optimum performance in the isomerization of alkyl aromatics using a catalyst comprising platinum on alumina plus mordenite, that the amount of alkali or alkaline earth metal cations in the mordenite should be adjusted to between 0.1 and 0.9 equivalents per gram atom of aluminum. It is disclosed in the 3,767,721 patent that below 0.1 equivalents the catalyst is too active and less selective, with destructive effects on the feedstock. It has been found, and contrary to the prior art, that hydrogen mordenite having a cation concentration below 0.1 equivalents can produce a highly active and selective catalyst. In order to obtain such a catalyst the ratio of silica to alumina in the hydrogen mordenite will be greater than the typical 9–11 to 1 but less than about 17 to 1. As will be seen in the examples below, catalysts of the invention have good activity and selectivity for isomerization of xylenes and isomerization of ethylbenzene to xylenes when the silica to alumina ratio of the hydrogen mordenite is about 14 to 1, but when the ratio is the typical value of 9–11 to 1 or as high as 17 to 1, the catalyst becomes unduly active, destructive, and unstable.

The composition of the catalyst of the invention may be varied, but broadly may be given as within the following limits:

| | |
|---|---|
| platinum | 0.1–1.0 wt.% |
| alumina support for platinum | 10–85 wt.% |
| hydrogen mordenite | 1–65 wt.% |
| binder or diluent | 0–80 wt.% |

Preferred compositions will include about 20–60 wt.% alumina, 0.3–0.4 wt.% platinum, 20–60 wt.% hydrogen mordenite, and up to about 60 wt.% diluent.

METHOD OF CATALYST PREPARATION

Various methods may be employed in order to produce the catalyst of the invention, aspects of which are illustrated in the four exemplary preparations given below. In each preparation the platinum component is deposited on an alumina support and then admixed with hydrogen mordenite.

EXAMPLE 1

Four hundred fifty grams of a predominantly gamma alumina (ignited basis) having a particle size characterized as 10 wt.%<10μ, 50 wt.%<23μ, and 90 wt.%<38μ is impregnated with a solution of 10.0 grams of 40% $H_2PtCl_6$ dissolved in 325 cc deionized $H_2O$. The wet powder is then transferred to a vacuum chamber and evacuated to 27 inches of Hg vacuum. Then $H_2S$ is bled into the chamber until a pressure of 5 inches of Hg is reached and then is maintained for 15 minutes. The vacuum is then released and the excess $H_2S$ is purged. The sulfided powder is then dried at 105° C. for 15–20 hours. After drying, the powder is then blended with a Patterson-Kelley V-blender for one-half hour with 550 grams of hydrogen mordenite (ignited basis) having a particle size characterized as 10 wt.%<2.2μ, 50 wt.%<5.8, and 90 wt.%<9.5μ. This mix is then transferred to a Perkins mixer and dry blended one hour. Deionized $H_2O$ is added to bring the moisture content to 30–35 wt.%, giving an extrudable mixture, which is extruded through a 0.063 inch diameter die and then dried at 105° C. for 16–20 hours. The finished extrudate is calcined in air free of organic compounds and flowing at 1000 vol air/hr/vol catalyst for a period of 2 hours at 105° C., and then 2 hours at 500° C.

EXAMPLE 2

Four hundred fifty grams of a predominantly gamma alumina (ignited basis) having a particle size averaging 25μ is impregnated with a solution of 10.0 grams of 40% $H_2PtCl_6$ dissolved in 325 cc deionized $H_2O$. The wet powder is then transferred to a vacuum chamber and evacuated to 27 inches of Hg vacuum. Then $H_2S$ is bled into the chamber until a pressure of 5 inches of Hg is reached and then is maintained for 15 minutes. The vacuum is then released and then the excess $H_2S$ is purged. The wet sulfided powder is then blended with a Patterson-Kelley V-mixer for one-half hour with 550 grams hydrogen mordenite (ignited basis) having a particle size averaging 6μ. This mix is transferred to a Perkins mixer and blended for 1 hour. Then, deionized $H_2O$ is added to bring the moisture content to 30–35 wt.% to give an extrudable mix. It is then extruded through a 0.063 inch diameter die and dried at 105° C. for 16–20 hours. The finished extrudate is then calcined in air free of organic compounds and flowing at 1000 vol air/hr/vol catalyst for a period of 2 hours at 105° C., and then 2 hours at 500° C.

EXAMPLE 3

Four hundred fifty grams of a predominantly gamma alumina (ignited basis) having a particle size averaging 6μ is impregnated with a solution of 10.0 grams of 40% $H_2PtCl_6$ dissolved in 325 cc deionized $H_2O$. The wet powder is then dried 16–20 hours at 105° C. The dry powder is then blended with a Patterson-Kelley V-mixer for ½ hour with 550 grams hydrogen mordenite (ignited basis) having a particle size averaging 7μ. This mix is then transferred to a Perkins mixer and dry blended for 1 hour. Then deionized $H_2O$ is added to bring the moisture content to 30–35% to give an extrudable mix. It is then extruded through a 0.063 inch diameter die and dried at 105° C. for 16–20 hours. The finished extrudate is then calcined in air free of organic compounds and flowing at 1000 vol air/hr/vol catalyst for a period of 2 hours at 105° C., and then 2 hours at 500° C.

EXAMPLE 4

Four hundred fifty grams of a predominantly gamma alumina (ignited basis) having a particle size averaging 23μ is impregnated with a solution of 10.0 grams of 40% $H_2PtCl_6$ dissolved in 325 cc deionized $H_2O$. The wet powder is then transferred to a vacuum chamber and evacuated to 27 inches of Hg vacuum. Then $H_2S$ is bled into the chamber until a pressure of 5 inches Hg is reached and then is maintained for 15 minutes. The sulfided powder is then dried at 105° C. for 16–20 hours. The dried powder is placed into a 4 liter beaker with 1 liter of deionized $H_2O$ and mixed for 1 hour. Then 550 grams of hydrogen mordenite (ignited basis) having a particle size averaging 6μ is added and the total volume brought to 3 liters with deionized water and mixed for 3 hours. Excess $H_2O$ is filtered off through #5 Whatman filter paper with vacuum and the mix is dried for 16–20 hours at 105° C. The dried mix is placed in a mixer and enough deionized $H_2O$ added to bring the moisture content to 30–35% giving an extrudable mix. It is then extruded through a 0.063 diameter die and dried at 105° C. for 16–20 hours. The finished extrudate is then calcined in air free of organic compounds at 1000 vol air/hr/vol catalyst for a period of 2 hours at 105° C., and then 2 hours at 500° C.

PERFORMANCE OF THE CATALYST

The catalyst of the invention is particularly useful in the commercially practiced Octafining process or other similar isomerization processes, wherein a hydrocarbon stream consisting essentially of a non-equilibrium mixture of $C_8$ aromatics is converted to a near-equilibrium mixture. A typical feedstream for such processes is prepared by solvent extraction and/or distillation and contains essentially only $C_8$ aromatics, that is, the three xylenes (para, meta, and ortho) and about 15–65 weight % of ethylbenzene. Since ethylbenzene will be in the range of only about 7–10 wt.% in equilibrium mixtures, it must be isomerized to xylenes or destroyed. The catalyst of the invention is capable of isomerizing ethylbenzene to xylenes rather than destroying it.

It is important to avoid destruction of the $C_8$ aromatics. In the commercially practiced process, paraxylene and orthoxylene are usually separated as products. Any unseparated $C_8$'s, including naphthenes, usually are returned to the isomerization reactor and recycled to extinction. Thus, while a high activity for isomerization is an important characteristic of the catalyst, selectivity, i.e., its ability to isomerize, but not destroy, $C_8$'s, is of special importance.

A catalyst prepared according to the invention provides superior performance when compared to catalysts of the prior art in contacting a mixed feed of xylenes and ethylbenzenes. Ideally, an isomerization catalyst causes both reactions, i.e., the isomerization of xylenes and the conversion of ethylbenzene to xylenes to approach their equilibrium values very rapidly. Such a catalyst is said to have high activity. The activity of a catalyst is indicated by the space velocity required to provide a given approach to equilibrium. The higher the space velocity, the greater the catalyst activity. For convenience, the activity is often reported as a percentage relative to a commercially available catalyst.

Knowing the composition of the feedstock and the products, approach to equilibrium is calculated from the following relationship:

$$X_i = \frac{F_i - P_i}{F_i - E_i}$$

where
$X_i$ = approach to equilibrium of a $C_8$ aromatic isomer, i (i.e., ethylbenzene and ortho, para, metaxylenes)
$F_i$ = concentration of i in the feed $C_8$ aromatics
$P_i$ = concentration of i in the product $C_8$ aromatics
$E_i$ = the equilibrium concentration of i in the $C_8$ aromatics (obtained from published values)

The equilibrium concentration of each of the four $C_8$ aromatics isomers is a constant value at any fixed temperature so that after measuring the composition of the feedstock and the reaction products, the approach to equilibrium can be calculated for each of the isomers. The rate at which the isomers approach equilibrium is expressed as a rate constant, which is dependent upon the space velocity.

For ethylbenzene (EB) the following relationship is used:

$$k_{EB} = -WHSV \ln(1 - X_{EB})$$

where
$k_{EB}$ = rate constant for ethylbenzene
WHSV = weight hourly space velocity
$X_{EB}$ = approach to equilibrium This equation will be recognized by those skilled in the art as a first order type of chemical reaction and was established by previous investigations to be valid. The relative activity values used in many of the following examples are obtained by dividing the k value for one catalyst by the value of k for a reference or standard catalyst at the same reaction conditions:

Relative Activity = $(k/k_{STANDARD}) \times 100$

The standard catalyst is arbitrarily given the value of 100. Higher values for a particular catalyst indicate that a given approach to equilibrium concentration was achieved at a higher space velocity, i.e., the catalyst is more active than the standard.

The rate at which paraxylene (PX) approaches equilibrium appears to follow a second order type of chemical reaction, and is calculated from the following relationship:

$$k_{PX} = WHSV \frac{X_{PX}}{1 - X_{PX}}$$

where
$k_{PX}$ = rate constant for paraxylene
WHSV = weight hourly space velocity
$X_{PX}$ = approach to equilibrium Once again, relative activity is calculated by dividing $k_{PX}$ for a catalyst by $k_{PX}$ for the reference catalyst.

While a catalyst should be active for isomerization of xylenes and conversion of ethylbenzene, it should not be active for competing reactions, particularly those that destroy $C_8$ aromatics. Such a catalyst is said to be selectively active for the isomerization of xylenes and the conversion of ethylbenzene. The selectivity of catalysts is indicated in the following examples as the percentage of the $C_8$ aromatics in the feedstock which remain at a specified approach to chemical equilibrium. Generally, $C_8$ aromatics will be lost by conversion to $C_1$–$C_5$ saturates and $C_6$–$C_7$ and $C_9$–$C_{10}$ aromatics. The amount of $C_8$ aromatics lost through competing reactions increases as chemical equilibrium is approached. A catalyst may be judged more selective and thus superior when for a given approach to chemical equilibrium it can isomerize xylenes and ethylbenzene with a higher yield of $C_8$ components when compared to other catalysts. Generally, selectivity is shown in the examples by reporting the percentage of $C_8$ aromatics from the feed remaining in the reactor product at a given approach to chemical equilibrium. More specifically, selectivity is expressed at a given approach to paraxylene equilibrium, since paraxylene is usually the preferred product. Obviously, retaining close to 100% of the $C_8$ aromatics is desired, since a value less than 100% indicates a loss of $C_8$ compounds, which are not converted to xylenes. The selectivity of the new catalysts is similar to or better than that of the prior art catalyst of U.S. Pat. No. 2,976,332. The activity of catalysts of the invention is substantially higher.

Platinum on alumina has been shown to have some activity for isomerization of xylenes as is shown in U.S. Pat. No. 3,078,318. However, many commercial feedstocks contain substantial amounts of ethylbenzene, which must be either converted to xylenes or destroyed in order to prevent its buildup in the recycle to the reactor from the paraxylene removal step. As has been previously mentioned, platinum on alumina is thought to hydrogenate ethylbenzene as a first step toward production of xylenes. However, platinum on alumina alone does not have any significant activity for conversion of ethylbenzene, as will be shown in the following example where pure ethylbenzene (EB) was reacted over a catalyst containing only platinum on active alumina and containing about 1 wt.% chloride.

EXAMPLE 5

| Wt. % Pt | Alumina | Relative Activity* EB | Products | | | |
|---|---|---|---|---|---|---|
| | | | Xylenes | Gas | Saturates | Toluene |
| 0.35 | gamma | 6 | 1–2% | 5% | 3% | 170% |

*compared to the prior art catalysts of Example 6 below, which have been assigned an EB activity of 100.

This reaction, which was carried out at 440° C., 12.9 atm, 1 WHSV, 8:1 H$_2$ to hydrocarbon ratio, produced little xylenes, but undesirable amounts of gas and toluene, suggested that the catalyst has activity for cracking and disproportionation of ethylbenzene.

For purposes of characterizing the reactions, a feed of 30 wt.% ethylbenzene (EB) and 70 wt.% metaxylene (MX) has been used in many of the examples which follow. (It may be noted that most commercial feeds contain more than the equilibrium amount of 7-10% but less than 30% ethylbenzene, as well as paraxylene and orthoxylene in addition to the metaxylene.) The catalyst of U.S. Pat. No. 2,976,332, which combines platinum on alumina and an amorphous silica alumina has been arbitrarily assigned the value of 100 for purposes of comparing the relative activities of catalysts of the invention, which are calculated as previously discussed. Except where specifically noted in the examples which follow, the activity of various catalysts for conversion of ethylbenzene to xylenes and for the isomerization of metaxylene to paraxylene is reported for standard reaction conditions of 427° C. and 13 atm, and with a H$_2$:hydrocarbon mol ratio of 8:1, the reaction being carried out with varying space velocities ranging between 1 and 8 WHSV (wt. C$_8$ aromatics/wt. catalyst/hr) for a period of about 120 hours.

When platinum on alumina is combined with other materials, substantial activity and selectivity for the conversion of ethylbenzene as well as for isomerization of xylenes is obtained. In Example 6 the prior art catalyst of U.S. Pat. No. 2,976,332, in which platinum on alumina is combined with an amorphous silica-alumina cracking catalyst, is given for two different alumina supports. In this example the feedstock was a mixture of 30% ethylbenzene and 70% metaxylene and the operating conditions for characterizing the catalysts of the invention were as previously discussed.

EXAMPLE 6

| Wt% Pt | Alumina | %Wt. Si-Al | Relative Activity | | Selectivity % Yield of C$_8$ aromatics at designated approach to PX equilibrium | | | |
|---|---|---|---|---|---|---|---|---|
| | | | EB | PX | 80% | 85% | 90% | 95% |
| 0.4 | eta | 50 | 100 | 100 | — | 92.3 | 91.3 | — |
| 0.4 | gamma | 50 | 63 | 83 | — | 92.1 | 91.3 | 86.7 |

It can be seen that addition of the acid component, amorphous silica-alumina, to platinum on alumina, produces a catalyst having substantial activity for converting ethylbenzene to xylenes as well as isomerization of metaxylene. Aluminas containing predominantly eta or gamma alumina are considered to have comparable performance, although the data of Example 6 suggests that use of an eta alumina support for platinum might be preferred. It should be noted that longer term tests have shown that catalysts using gamma alumina may be expected to have greater stability and that over a working cycle between regenerations, the apparent initial activity advantage for eta alumina shown in Example 6 may not be retained. Further, to the user, the selectivity of such catalysts is significantly more important than their activity and in that respect the two catalysts are essentially the same. Such catalysts are the standard to which the new catalysts of the invention are compared.

Platinum on alumina is combined with varying amounts of hydrogen mordenite as required to adjust the performance of the catalyst. Increasing the amount of hydrogen mordenite improves the relative activity of the new catalyst as compared to the standard catalyst of Example 6. However, beyond the stated range of hydrogen mordenite content, the yield of C$_8$ aromatics (an indication of selectivity since it reflects losses by cracking, disproportionation, etc.) decreases as the amount of hydrogen mordenite is increased. Since both high activity and high yields are desired, the amount of hydrogen mordenite must be optimized. Between 25 and 50 wt.% hydrogen mordenite would appear to be suitable for a typical commercial C$_8$ aromatics isomerization unit. But a wider range of compositions is possible, as previously noted. Further additional amounts of alumina and/or silica-alumina (without platinum deposited thereon) may be included if desired.

Platinum or another hydrogenation-dehydrogenation component is considered necessary for conversion of ethylbenzene. In a typical catalyst of the invention 0.4 wt.% Pt on the finished catalyst is used. However, smaller amounts of platinum may be effective. For commercial use, a platinum content of 0.3-0.4 wt.% would be preferred as being a practical balance of performance and cost. Larger amounts of platinum would be expected to retain high activity for a long period, but at increased cost. Smaller amounts would be expected to lose high activity and selectivity sooner, thus requiring more frequent regeneration and having a shorter life, although having a lower initial cost.

Platinum is, however, important to a viable catalyst composite as will be seen in Example 7, in which it is shown that a catalyst combining alumina and hydrogen mordenite (H-M), but containing no platinum, has a substantially inferior performance compared to a catalyst of the invention.

EXAMPLE 7

| Wt.% Pt | Alumina | %H-M | Approach to Equilibrium at 4.7 WHSV | | Selectivity % Yield of C$_8$ aromatics at designated approach to PX equilibrium | | | |
|---|---|---|---|---|---|---|---|---|
| | | | EB | PX | 78% | 80% | 83% | 85% |
| 0 | gamma | 40 | 16.5 | 80 | 90 | 86 | 78 | — |
| 0.4 | gamma | 35 | 40 | 84.5 | — | 92.6 | — | 89.8 |

It is evident that, without platinum, ethylbenzene conversion is significantly reduced, although activity for xylene isomerization is retained. In this example activity is given as percentage approach to equilibrium for a given space velocity and not as percentage relative to the catalyst of Example 6. It may be noted that this method of reporting activity was made necessary because the apparent reaction order for catalysts containing no platinum differs from those containing platinum. Selectivity of a catalyst containing no platinum is much poorer, that is, losses of C$_8$ aromatics are higher for any given approach to paraxylene equilibrium.

The method of combining the components of the catalyst has an important effect on the performance of the finished catalyst. Example 8 compares two catalysts prepared by combining hydrogen mordenite with platinum on alumina in the same proportions, Catalyst A having the platinum deposited solely on the alumina and Catalyst B in which a mixed base is impregnated with platinum. The reaction conditions and feed compositions were the same as those generally used to characterize the catalysts and more specifically those of Example 6. Substantially inferior performance is shown when impregnation is done on a combined bases (B) compared with the catalyst of the invention (A), in which the platinum is deposited solely on the alumina.

EXAMPLE 8

| Catalyst | Wt.% Pt | alumina | %H-M | Relative Activity | | Selectivity | | | |
|---|---|---|---|---|---|---|---|---|---|
| | | | | | | % Yield of C$_8$ aromatics at designated approach to PX equilibrium | | | |
| | | | | EB | PX | 80 | 85 | 90 | 95 |
| A | 0.4 | gamma | 20 | 152 | 187 | 93.6 | 91.6 | 89.2 | 85.4 |
| B | 0.4 | gamma | 20 | 56 | 104 | 88.6 | 84.3 | 78.9 | 72.9 |

The prior art and in particular U.S. Pat. No. 3,767,721, has reported that control of the cation content of the mordenite is important if a catalyst is to be produced having the best selectivity and specifically that the alkali and alkaline earth metal cation level (hereinafter "cation") should be greater than 0.1 equivalents per gram atom of aluminum. Surprisingly, we have found that very satisfactory catalysts can be made with mordenite having quite low cation content (0.026 gram-equivalent cation/gram-equivalent Al) while catalysts made with mordenite having 0.2 gram-equivalent cation/gram-equivalent Al have a higher conversion but at the expense of greater C$_8$ losses. The ratio of silica to alumina in the mordenite will be shown to account for this unexpected result.

Example 9 reports the performance of catalyst C prepared according to the present invention with catalyst D, prepared in a manner similar to that of the 3,767,721 patent. Two feedstocks, ethylbenzene (EB) and orthoxylene (OX), were used and the results are reported in terms of the feedstock conversion and the losses of C$_8$ molecules (rather than retention of C$_8$'s as in many of the other examples). The reaction was carried out at 427° C., 12.9 atm., a H$_2$/hydrocarbon ratio of 8/1, and space velocities of 1 WHSV for ethylbenzene and 3.2 WHSV for orthoxylene.

It will be evident from examination of the results shown that the catalyst of the 3,767,721 patent (D) has a greater activity than the present catalyst (C) but is less selective, as is shown by the substantial increases in C$_8$ losses. Example 9 suggests that the catalyst of the prior art (D) is undesirably active since high losses of C$_8$'s occur while the catalyst prepared at a low cation level taught to be unacceptable by the prior art gives a more desirable combination of activity and C$_8$ yield. This result is contrary to that expected from the teachings of U.S. Pat. No. 3,767,721.

The apparent contradiction may be explained in the light of our discovery that the ratio of silica to alumina is an important characteristic of mordenites used in catalysts for isomerization of alkyl aromatics. The catalysts reported in U.S. Pat. No. 3,767,721 were made with mordenite having silica to alumina ratios of 9.8:1 and 10.5:1. The patentees found that an excessively active catalyst was produced having poor selectivity for the isomerization of xylenes and conversion of ethylbenzene to xylenes when the mordenite contained less than 0.1 gm-equiv. of cations per gm-equiv. of aluminum. Consequently, the patentees did not use hydrogen mordenite, which has a low cation content, but only partially dealkalized the sodium mordenite to optimize activity of their catalyst. They limited their invention to catalysts made with mordenite having a range of 0.1 to 0.9 gm-equiv. of cations per gm-equiv. of aluminum. In contrast, catalysts of the present invention are made with mordenite having an average SiO$_2$/Al$_2$O$_3$ ratio of about 14 to 1. With such catalysts, a hydrogen mordenite containing only small amounts of cations can be used and in fact is preferred.

In the following Example 10 the performance of catalysts made with mordenite having differing silica to alumina ratios show the significance of this ratio.

Each of the catalysts in Example 10 has a cation content at or below 0.1 and thus would be expected to be highly active and destructive of the C$_8$ aromatics, that is, have a low yield. The performance of catalyst E which has a silica/alumina ratio in the nominal range of synthetic mordenite is distinctly inferior to that of catalyst F which has a silica/alumina ratio of 14.4:1. The performance of catalyst G made with hydrogen mordenite having a silica to alumina ratio of 17:1 is clearly unacceptable. Catalysts E and G have higher relative activity than the catalyst of the invention (F), but such high activity is obtained by destroying C$_8$ aromatics, as can be seen from the poor selectivities. The selectivity of catalyst F is superior. It will be recalled that selectivity is considered particularly important to the user of these catalysts. This may be explained by considering the relative values of the catalyst and the feedstock which is passed over the catalyst during its useful life. The value of C$_8$ aromatics destroyed by a less selective but more active catalyst is much greater than the saving made by purchase of a smaller quantity of such a catalyst. The user of these catalysts would consider catalysts E and G to be commercially unacceptable when compared to catalyst F. While not apparent from the data of Example 10, the relative activity of an excessively active catalyst such as E changes rapidly during the first few hours of operation. The values reported are taken from near the end of a 57 hour test. Catalysts of the invention, such as catalyst F, typically have essentially a constant relative activity and do not show the unstable performance of catalyst E. Catalyst G was so active that, at the highest space velocity used for the tests (8 WHSV), the analysis of the reaction products

EXAMPLE 9

| Catalyst | Wt.% Pt | Alumina | Wt.% H-M | Mol Ratio SiO$_2$/Al$_2$O$_3$ | Cation Content | | EB feed | | OX feed | |
|---|---|---|---|---|---|---|---|---|---|---|
| | | | | | Wt.% | Gm-Equiv. Cation/gm-equiv Al | % Conv. | C$_8$ loss | % Conv. | C$_8$ loss |
| C | 0.4 | gamma | 55 | 14.4 | 0.03 | 0.026 | 83.6 | 42.5 | 74.3 | 14.6 |
| D | 0.4 | gamma | 55 | 11.5 | 1.2 | 0.21 | 98.3 | 76.5 | 84.5 | 31.6 | indicated that chemical equilibrium was closely approached and the reaction rate was too rapid to be computed. As a consequence, the relative activity could not be calculated. The selectivity figures are taken from an extrapolation of the available data and are presented only for an approximate comparison with the other two catalysts.

EXAMPLE 10

| Catalyst | HM Mol Ratio $SiO_2/Al_2O_3$ | Relative Activity EB | Relative Activity PX | Selectivity % Yield of $C_8$ Aromatics at Designated Approach to PX Equilibrium 85 | 90 | 92 |
|---|---|---|---|---|---|---|
| 25 wt.%–1.6% Pt on gamma alumina 25 wt.%-gamma alumina 50 wt.%-HM (0.01 $\frac{\text{gm-equiv cation}}{\text{gm-equiv Al}}$) | 10.7:1 | 535 | 523 | 87.2 | 78 | 73 |
| 45 wt.%–0.8% Pt on gamma alumina 55 wt.%-HM (0.1 $\frac{\text{gm-equiv cation}}{\text{gm-equiv Al}}$) | 14.4:1 | 209 | 254 | 92.8 | 89.9 | 87.5 |
| 25 wt.%–1.6% Pt on gamma alumina 25 wt.%-gamma alumina 50 wt.%-HM (0.02 $\frac{\text{gm-equiv cation}}{\text{gm-equiv Al}}$) | 17:1 | too high to measure | | 65 | 55 | 50 |

Catalysts of the invention are more active (but still selective for isomerization) when the mordenite contains less than 0.1 gram-equivalents of cations per gram-atom of aluminum and in this respect such catalysts are distinguished from the disclosures of the prior art. However, the cation content may equal or exceed 0.1 gram-equivalents if the performance of the resulting catalyst is acceptable, despite the reduction in isomerization activity which would be expected. The lowering of relative activity found in catalysts containing mordenite having cations in amounts above 0.1 gm-equivalents is seen in Example 11, where all the catalysts contain mordenite having a silica/alumina ratio of about 14:1 and differ mainly in the amount of cations present. It is typical of synthetic mordenites that they contain principally sodium cations, although others such as calcium and magnesium may be present in smaller amounts. Whereas in previous examples the cation content of the mordenite was principally sodium, in Example 11 the cation content includes substantial amounts of calcium and magnesium to provide a relatively large total cation content.

EXAMPLE 11

| Catalyst | Total Cation Content gm-equiv/gm-equiv Al | Relative Activity |
|---|---|---|
| 25 wt.%–1.6% Pt on gamma alumina 25 wt.%-gamma alumina 50 wt.%-HM | 0.10 | 274 |
| 25 wt.%–1.6% Pt on gamma alumina 25 wt.%-gamma alumina 50 wt.%-HM | 0.28 | 189 |
| 25 wt.%–1.6% Pt on gamma alumina 25 wt.%-gamma alumina 50 wt.%-HM | 0.44 | 128 |

It can be seen that the relative activity of the catalyst will fall to 100 at about 0.5 gm-equivalents of total cations. At such an activity level the catalyst would have little advantage over catalysts of the prior art. Thus 0.3 gram-equivalents of cations per gram-atom of aluminum would be a maximum value for a commercially acceptable catalyst according to the invention, although the economics of the process would indicate that the most active catalyst should be produced which has good selectivity for $C_8$ isomerization. This may be done according to the invention by using hydrogen mordenite having a cation level below 0.1 gm-equivalents.

For use in a catalyst of the invention the alumino-silicate should (1) have an X-ray diffraction pattern characteristic of mordenite, (2) have a cation level below about 0.3 gm equiv/gm-equiv. Al, usually below 0.1 and (3) have a silica to alumina ratio greater than the nominal ratio of 9-11:1, in the vicinity of about 14:1 but less than about 17.

In the region between silica to alumina ratios of about 9-11:1 and about 17:1, one skilled in the art would be expected to be able to adjust the cation level as required to accommodate the effect of the silica to alumina ratio. Catalysts made according to the present invention are preferably made with mordenite having a silica/alumina mol ratio about 14:1 and a cation content below 0.1 gm-equiv./gm-equiv. aluminum.

Catalysts of the invention appear to have improved ability compared to catalysts of the prior art to retain activity after extended use and further, to retain high activity even after regeneration. These properties are illustrated in the following Example 12 in which a typical commercial feedstock containing mixed xylenes and ethylbenzenes was reacted over a commercial catalyst containing silica-alumina (H) and a catalyst of the invention (I).

EXAMPLE 12

| Catalyst | Component Reacted | Relative Activity at 100 hrs. | Relative Activity at 300 hrs. | Stability (300/100) | Selectivity % Yield of $C_8$ Aromatics at 95% Approach to Equilibrium |
|---|---|---|---|---|---|
| 0.4% Pt on 50% eta alumina; 50% silica-alumina all by weight | EB | 100 | 51 | 0.51 | 90.7 |
|  | xylenes | 100 | 67 | 0.67 | |
| 0.4% Pt on 45% eta alumina; 45% H-mordenite ($SiO_2/Al_2O_3$ = 14.4:1) | EB | 160 | 120 | 0.75 | 90.7 |

-continued

| Catalyst | Component Reacted | Relative Activity at 100 hrs. | Relative Activity at 300 hrs. | Stability (300/100) | Selectivity % Yield of $C_8$ Aromatics at 95% Approach to Equilibrium |
|---|---|---|---|---|---|
| (0.032 $\frac{\text{gm-equiv cation}}{\text{gm-equiv Al}}$; 10% silica alumina, all by weight | xylenes | 490 | 440 | 0.90 | |
| Same as (I) above after regeneration | EB xylenes | 160 520 | 140 560 | 0.88 1.10 | 95 |

The tests were carried out at 454° C. and 12.9 atm pressure, a space velocity of 4 WHSV, and a hydrogen to hydrocarbon mol ratio of 10:1. The above data indicate that the performance of a catalyst of the invention after regeneration may be equal to or even better than the same catalyst as freshly prepared. The stability of the catalyst of the invention is shown to be better than that of the catalyst of the prior art, which used amorphous silica-alumina instead of hydrogen mordenite. It is of importance that the catalyst has improved stability with regard to ethylbenzene since it has been found that in commercial operation the loss of catalytic activity for conversion of ethylbenzene establishes when regeneration of the catalyst is required. Thus the catalyst of the invention should have a longer average cycle length.

It should be noted that the minor fraction of amorphous silica-alumina used in preparation of the catalyst of this example was included principally for convenience in the preparation. It is within the scope of the invention to include alumina which does not support platinum and/or amorphous silica-alumina along with the principal constituents in amounts up to about 80 wt.% of the total catalyst.

The foregoing discussion and examples are provided to instruct one skilled in the art to understand and to use the invention. It should not be considered to limit the invention, which is defined by the claims which follow.

What is claimed is:

1. A process for isomerizing $C_8$ alkyl aromatic compounds including ethylbenzene in amounts greater than the equilibrium amount comprising passing said alkyl aromatic compounds and hydrogen under isomerizing conditions over a catalyst and producing a near equilibrium amount of mixed xylenes and ethylbenzene, said catalyst consisting essentially of:
   (a) a catalytically active amount of a component selected from the group consisting of platinum and platinum plus one or more of palladium, ruthenium, rhodium, iridium, and rhenium, deposited on particulate alumina; and
   (b) particulate hydrogen mordenite containing less than 0.1 gram equivalent of alkali and alkaline earth metal cations per gram atom of aluminum and having a silica to alumina ratio greater than about 9-11 to 1 and less than about 17 to 1, said component on particulate alumina of (a) and said particulate hydrogen mordenite of (b) being prepared separately and thereafter combined to produce said catalyst.

2. The process of claim 1 wherein the hydrogen mordenite has a silica to alumina mol ratio of about 14 to 1.

* * * * *

UNITED STATES PATENT AND TRADEMARK OFFICE
CERTIFICATE OF CORRECTION

PATENT NO. : 4,128,591

DATED : December 5, 1978

INVENTOR(S) : CARR, POLINSKI, HINDIN and KOSCO

It is certified that error appears in the above-identified patent and that said Letters Patent are hereby corrected as shown below:

In column 5, line 38, after the numeral "5.8" and before the comma "," insert the symbol --$\mu$--..

In Column 8, line 65, in Example 5, under the heading "Toluene", the number "170%" should be deleted and replaced by --17%--.

In Column 10, line 25, the word "long" should be replaced by --longer--.

In Example 10, Column 13, lines 9 through 21, under the heading "Catalyst", the letter designations for each Catalyst described should be inserted as shown below:

UNITED STATES PATENT AND TRADEMARK OFFICE
CERTIFICATE OF CORRECTION

PATENT NO. : 4,128,591

DATED : December 5, 1978

INVENTOR(S) : CARR, POLINSKI, HINDIN and KOSCO

It is certified that error appears in the above-identified patent and that said Letters Patent are hereby corrected as shown below:

Catalyst

E    25 wt.%-1.6% Pt on gamma alumina
     25 wt.%-gamma alumina
     50 wt.%-HM (0.01 $\frac{\text{gm-equiv cation}}{\text{gm-equiv Al}}$)

F    45 wt.%-0.8% Pt on gamma alumina
     55 wt.%-HM (0.1 $\frac{\text{gm-equiv cation}}{\text{gm-equiv Al}}$)

G    25 wt.%-1.6 Pt on gamma alumina
     25 wt.%-gamma alumina
     50 wt.%-HM (0.02 $\frac{\text{gm-equiv cation}}{\text{gm-equiv Al}}$)

UNITED STATES PATENT AND TRADEMARK OFFICE
CERTIFICATE OF CORRECTION

PATENT NO. : 4,128,591

DATED : December 5, 1978

INVENTOR(S) : CARR, POLINSKI, HINDIN and KOSCO

It is certified that error appears in the above-identified patent and that said Letters Patent are hereby corrected as shown below:

In Example 12, columns 13 and 14, lines 60 to 70, under the heading "Catalyst", the letter designations for each catalyst described should be inserted as shown below Catalyst H    0.4% Pt on 50% eta alumina;
50% silica-alumina
all by weight I    0.4% Pt on 45% eta alumina;
45% H-mordenite
($SiO_2/Al_2O_3$ = 14.4:1)
(0.032 $\frac{\text{gm-equiv cation}}{\text{gm-equiv Al}}$;
10% silica alumina,
all by weight Signed and Sealed this Third Day of July 1979

[SEAL]

Attest:

*Attesting Officer*

LUTRELLE F. PARKER
*Acting Commissioner of Patents and Trademarks*